July 12, 1966 L. LENS Plant Pat. 2,657
ROSE PLANT
Filed Oct. 13, 1964
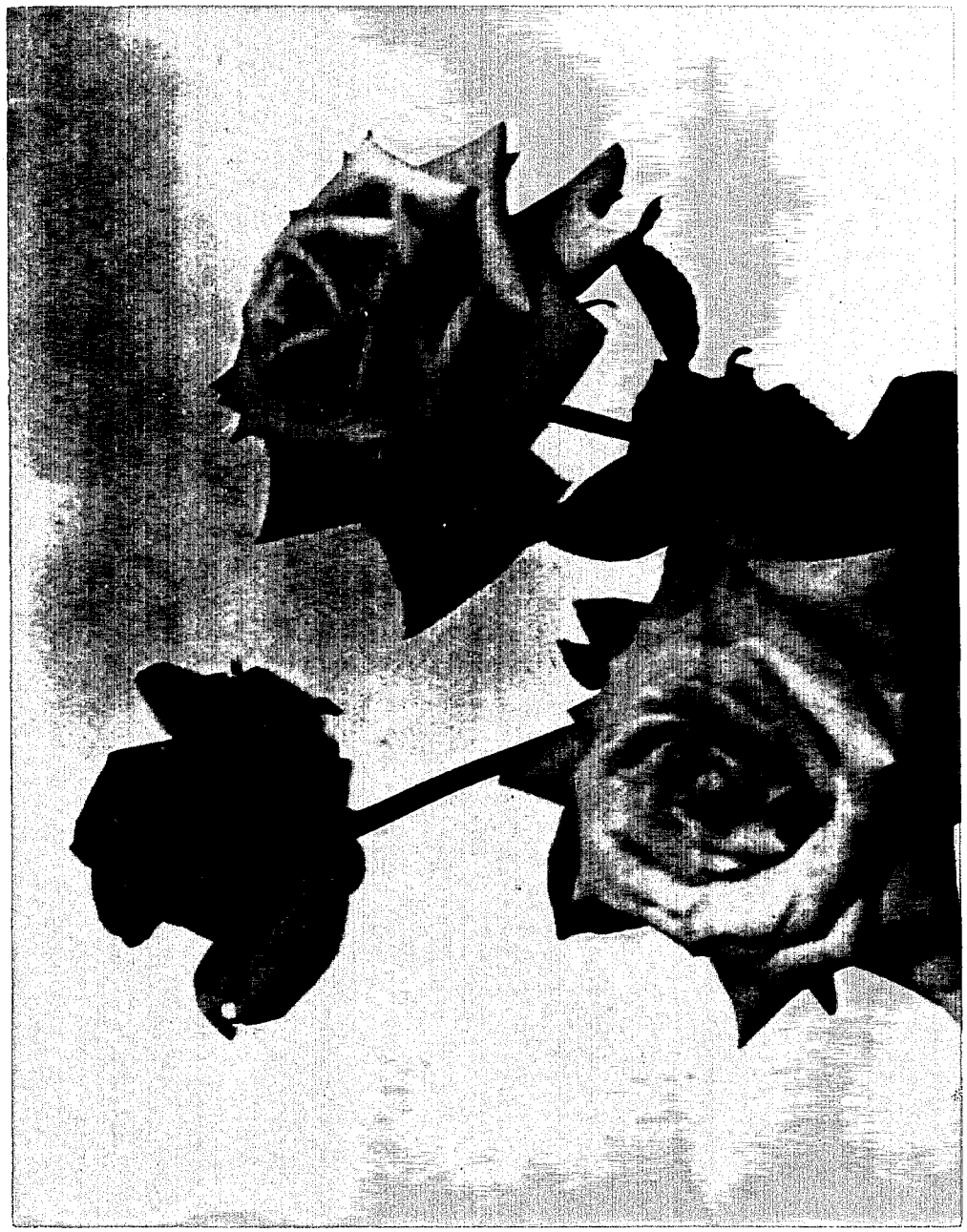
Inventor.
Louis Lens
By: Robb & Robb
Attorneys.

United States Patent Office

Plant Pat. 2,657
Patented July 12, 1966

2,657
ROSE PLANT

Louis Lens, Wavre-Notre-Dame, Belgium, assignor, by direct and mesne assignments, of one-half to McHutchison & Co., Inc., Ridgefield, N.J., a corporation of New Jersey, and one-half to San Lorenzo Nursery Company, San Leandro, Calif., a corporation of California

Filed Oct. 13, 1964, Ser. No. 403,672
Claims priority, application Belgium Oct. 15, 1963
1 Claim. (Cl. Plt.—20)

The present invention relates to a new and distinct variety of rose plant of the hybrid tea class which was originated by crossing the rose variety known as "Fandango" (U.S. Plant Patent No. 894) with an unnamed and unpatented seedling derived from a cross of the variety "Independence" (U.S. Patent No. 1,036) with an unnamed and unpatented seedling of "Lady Sylvia" (unpatented) × "Independence."

The primary objective of this breeding was to produce a new and improved rose variety of the hybrid tea class, which would be especially suitable for cut flower culture under glass, and which overcomes the major faults of prior cut flower varieties. This objective was fully achieved, along with other desirable improvements, as evidenced by the following unique combination of characteristics which are outstanding in my new variety and which distinguish it from its parents, as well as from all other varieties of which I am aware:

(1) A healthy and vigorous plant habit;

(2) Production of strong lateral branches on the plant which bear heavy dark green foliage;

(3) A small leaf size;

(4) Strong, upright and stiff flower stems;

(5) Excellent production of large flowers having stiff petals and good form when grown in greenhouses for cut flowers;

(6) A distinctive, attractive and Brilliant Mandarin Red flower color which is retained until the flowers fall; and (7) Long lasting flower qualities as cut flowers when kept in water.

Asexual reproduction of my new rose variety by both grafting and budding, as performed by me at Wavre-Notre-Dame, Belgium, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart, issued by the British Colour Council in collaboration with the Royal Horticultural Society, except where general color terms of ordinary dictionary significance are obvious:

Type: Hardy; dwarf; bush; greenhouse; seedling; for cut flower production.

Class: Hybrid tea.

Breeding: Seedling.

*Seed parent.*—"Fandango."

*Pollen parent.*—An unnamed seedling of "Independence" with an unnamed seedling of "Lady Sylvia" × "Independence."

Propagation: Holds its distinguishing characteristics through succeeding propagations by both grafting and budding.

*Flower*

Locality where grown and observed: Wavre-Notre-Dame, Belgium.

Flowers borne: Singly; on strong stems of medium length.

Quantity of bloom: Moderate, in greenhouse.

Continuity: Continuous.

Fragrance: None.

Bud:

*Peduncle.*—Long; stiff; smooth. Color—grey.

*Before calyx breaks.*—Size—medium large. Form—long; pointed; with foliaceous parts extending beyond the tip of the bud equal to ½ or more of its length. Color—Geranium Lake, Plate 20.

*As calyx breaks.*—Color—Geranium Lake, Plate 20.

*As first petal opens.*—Size—medium large. Form—long; pointed. Color: Outside—Geranium Lake, Plate 20; inside—Mandarin Red, Plate 17.

*Opening.*—Opens up well; not influenced by wet or warm weather.

Bloom:

*Size (when fully open).*—Medium large; from 3 inches to 4 inches.

*Petalage.*—Double, but stamens not hidden; from 28 to 32 petals; arranged regularly.

*Form.*—Cupped and high-centered at first and remaining high-centered; petals being at first tightly rolled outward and remaining tightly rolled outward at maturity.

Petals:

*Texture.*—Thick; stiff; leathery.

*Appearance.*—Inside—velvety. Outside—dull.

*Shape.*—Outer—round. Intermediate—round. Inner—round.

This description of a newly opened flower was made from a rose grown in a greenhouse during the month of September at Wavre-Notre-Dame, Belgium:

*Color.*—Outer petal: Outside surface—Mandarin red, Plate 17; inside surface—Very brilliant Mandarin Red, Plate 17. Intermediate petal: Outside surface—Very Brilliant Mandarin Red, Plate 17; inside surface—Very Brilliant Mandarin Red, Plate 17. Inner petal: Outside surface—Very Brilliant Mandarin Red, Plate 17; inside surface—Very Brilliant Mandarin Red, Plate 17.

This description was made of a rose that was open for three days in a greenhouse during the month of September at Wavre-Notre-Dame, Belgium:

*Color.*—Outer petal: Outside surface—Brilliant Mandarin Red, Plate 17; inside surface—Brilliant Mandarin Red, Plate 17. Inner petal: Outside surface—Brilliant Mandarin Red, Plate 17; inside surface—Brilliant Mandarin Red, Plate 17.

*General color effect.*—Newly opened flower—Brilliant Mandarin Red, Plate 17. 3-days open—Brilliant Mandarin Red, Plate 17.

*Behavior.*—Persists; fading brown-purple.

*Flower longevity.*—On bush in garden—10 days during July and August. Cut roses grown in greenhouse and kept at livingroom temperatures—10 days during July and August.

*Reproductive organs*

Stamens: Few; arranged irregular. Color—light yellow.

Filaments: From short to medium length. Color—reddish.

Anthers: From small to medium size. Color—yellow bordered, with reddish center.

Pollen: Sparse. Color—lemon.
Pistils: Few.
Styles: Short; uneven length; bunched; columnar.
Stigma: White yellow.
Ovaries: Some protruding from calyx.
Hips: From ovoid to globular; with pear shaped neck; smooth; walls thick and fleshy. Color—orange yellow.
Sepals: Permanent; short; curled. Color—olive green.
Seeds: Very few.

*Plant*

Foliage:

*Leaves.*—Compound of 3, 5 or 7 leaflets; moderately abundant; small size; heavy; leathery.

*Leaflets.*—Shape—oval pointed. Margin—Simply serrated, with serrations being large and sharp.

*Color.*—Mature: Upper surface—Ivy Green, Plate 0001064/2; under surface—Spinach Green, Plate 0960/3. Young: Upper surface—Erythrite Red, Plate 0027/1; under surface—Garnet Brown, Plate 00918/2.

*Rachis (the supporting stem of the compound leaf).*—Light. Upper side—hairy. Under side—hairy.

*Stipules.*—Short; narrow.

*Disease resistance.*—Normal resistance to the usual rose diseases when grown in the greenhouse, but susceptible to blackspot when grown outdoors, as determined by comparison with other varieties grown under comparable conditions at Wavre-Notre-Dame, Belgium.

Growth:

*Habit.*—Bushy; upright.

*Growth.*—Free; vigorous.

*Canes.*—Heavy; attain height of from 2 to 3 feet.

*Main stems.*—Color—bright brown. Thorns—many; hooked downward. Prickles—few. Hairs—none.

*Branches.*—Color—bright grey green. Thorns—many; medium length; hooked downward. Prickles—none. Hairs—none.

*New shoots.*—Color—Erythrite Red, Plate 0027/1. Thorns—many. Color—Erythrite Red, Plate 0027/2. Prickles—none. Hairs—none.

I claim:

A new and distinct variety of rose plant of the hybrid team class, substantially as herein shown and described, characterized particularly as to novelty by the unique combination of a healthy and vigorous plant habit, production of strong lateral branches on the plant which bear heavy dark green foliage, a small leaf size, strong, upright and stiff flower stems, excellent production of large flowers having stiff petals and good form when grown in greenhouses for cut flowers, a distinctive, attractive and Brilliant Mandarin Red flower color which is retained until the flowers fall, and long lasting flower qualities as cut flowers when kept in water.

No references cited.

ABRAHAM G. STONE, *Primary Examiner.*

ROBERT E. BAGWILL, *Assistant Examiner.*